(12) United States Patent
Zafar et al.

(10) Patent No.: US 11,175,281 B2
(45) Date of Patent: Nov. 16, 2021

(54) WELL PLATE COVER WITH EMBEDDED ELECTRONIC SENSORS FOR MONITORING CELL METABOLISM

(71) Applicant: International Business Machines Corporation, Armonk, NY (US)

(72) Inventors: Sufi Zafar, Briarcliff Manor, NY (US); Norma E. Sosa, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 349 days.

(21) Appl. No.: 16/108,040

(22) Filed: Aug. 21, 2018

(65) Prior Publication Data

US 2020/0064336 A1    Feb. 27, 2020

(51) Int. Cl.
| | |
|---|---|
| *G01N 27/00* | (2006.01) |
| *G01N 33/50* | (2006.01) |
| *G01N 33/84* | (2006.01) |
| *C12M 1/32* | (2006.01) |
| *B01L 3/00* | (2006.01) |

(52) U.S. Cl.
CPC ...... *G01N 33/5038* (2013.01); *B01L 3/50853* (2013.01); *C12M 23/12* (2013.01); *G01N 33/84* (2013.01); *B01L 2300/0829* (2013.01)

(58) Field of Classification Search
CPC .............. G01N 33/84; G01N 33/5005; G01N 33/5438; G01N 21/80
USPC ........................................... 422/62.02, 82.01
See application file for complete search history.

(56) References Cited

U.S. PATENT DOCUMENTS

| | | | |
|---|---|---|---|
| 8,679,426 | B2 | 3/2014 | Barrett |
| 9,170,255 | B2 | 10/2015 | Teich |
| 2012/0301913 | A1 | 11/2012 | Youngbull |
| 2014/0273191 | A1 | 9/2014 | Tipgunlakant |
| 2015/0072375 | A1 | 3/2015 | Barros Olmedo |
| 2016/0011216 | A1* | 1/2016 | Feller .................. G01N 27/4145 436/501 |

OTHER PUBLICATIONS

Piet Bergveld, ISFET, Theory and Practice, IEEE Sensor Conference Toronto, Oct. 2003, pp. 1-26.
Seahorse Bioscience, The Cancer-Metabolism Link, Cell Metabolism Assays for Cancer Research, Aug. 1, 2016, pp. 1-6.

* cited by examiner

*Primary Examiner* — Natalia Levkovich
(74) *Attorney, Agent, or Firm* — L. Jeffrey Kelly; Otterstedt, Wallace & Kammer, LLP

(57) ABSTRACT

A testing system includes a well cover portion, a sensor portion extending from the well cover portion, a sensing surface disposed on the sensor portion, a conducting wire extending through the sensor portion and contacting the sensing surface, a transducer connected to the conducting wire, and a reference electrode extending through the well cover portion.

20 Claims, 4 Drawing Sheets

WELL PLATE COVER WITH EMBEDDED ELECTRONIC SENSORS FOR MONITORING CELL METABOLISM

The present disclosure relates generally to electronic sensors, and more particularly to a well plate cover having an embedded electronic sensor.

Existing methods for measuring the metabolism of cancer cells include optical sensors.

BRIEF SUMMARY

According to an embodiment of the present invention, a testing system includes a well cover portion, a sensor portion extending from the well cover portion, a sensing surface disposed on the sensor portion, a conducting wire extending through the sensor portion and contacting the sensing surface, a transducer connected to the conducting wire, and a reference electrode extending through the well cover portion.

According to one or more embodiments of the present invention, a testing system comprises a well cover portion, a conducting wire extending through the well cover portion, a sensing surface electrically connected to the conducting wire, a transducer connected to the conducting wire, and a reference electrode extending through the well cover portion.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide for:

- an electronic label-free sensor for measuring characteristics of suspended cells (e.g., cancer cells), with high resolution and at a low cost (for example, as compared to optical sensors).

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

According to one or more exemplary embodiments of the present invention, an electronic label-free sensor is embedded in a well plate cover. According to one or more exemplary embodiments of the present invention, a cover plate comprises one or more embedded electronic sensors to measure pH and other analytes in real time during cell metabolism. For example, cancer cells typically have a higher metabolism than a healthy cell that causes an extracellular medium to have lower pH (i.e., more acidic). Monitoring cancer cell metabolism is important to discovery methods for new medicines, etc.

According to one or more exemplary embodiments of the present invention, an electronic label-free sensor enables measurements of suspended cells (e.g., cancer cells), with high resolution and at a low cost (for example, as compared to optical sensors).

Embodiments described herein are applicable to attached cells and cells suspended in a medium (e.g., a culture medium).

Figure 1:
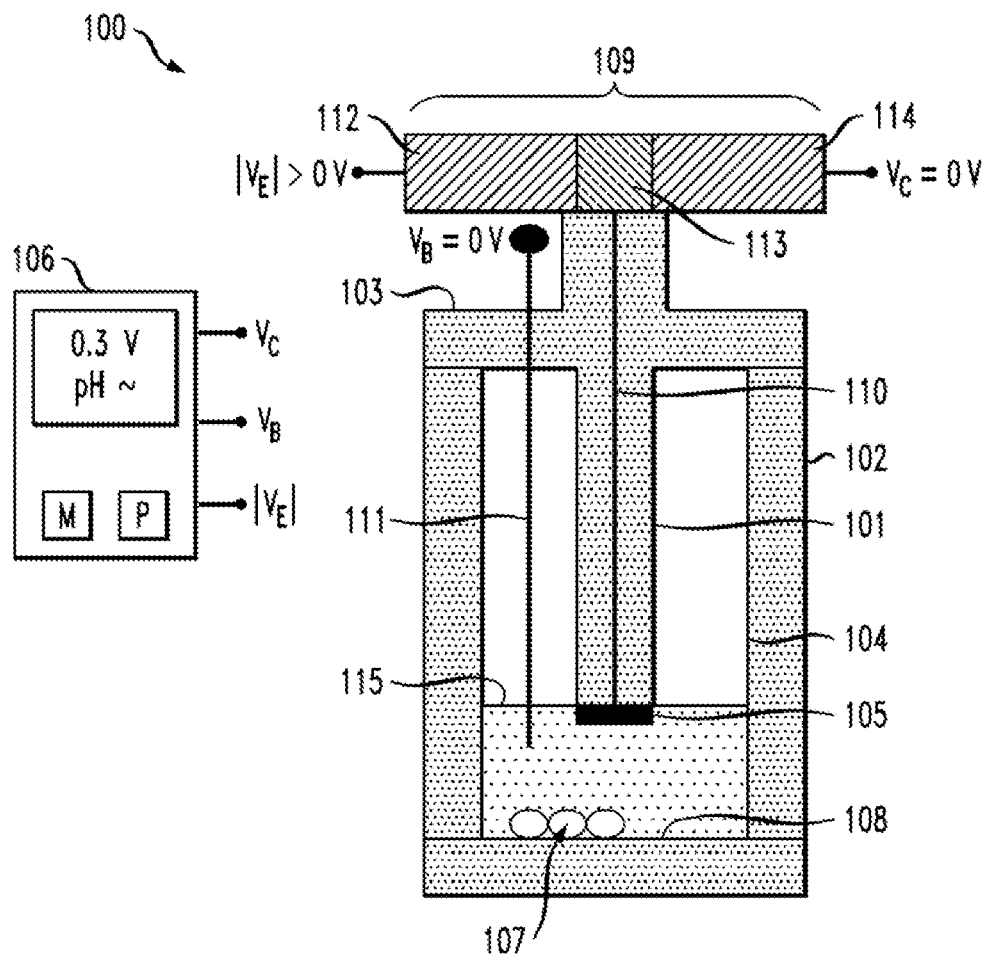
FIG. 1 depicts a view of a first well cover having an embedded sensor for measuring a characteristic of attached cells according to an embodiment of the present invention.

Attached Cells:

According to an exemplary embodiment of the present invention and referring to FIG. 1, a testing system 100 comprises a first well cover 103, an embedded sensor portion 101 including a sensing surface 105 and a conducting wire 110, a bipolar junction transistor (BJT) transducer 109 with its base 113 electrically connected to the conducting wire 110 and the sensing surface 105, and a reference electrode 111.

According to exemplary embodiments of the present invention, to measure pH or H+ concentration changes in the solution 115, a voltage $|V_E|>0$ V is applied to the emitter 112 of the BJT 109, collector ($V_C$) and reference ($V_B$) voltages are set at 0 V. Using these applied voltages, the collector current $I_C$ (i.e., a sensing signal current), is measured as a function of time (e.g., over about an hour, with measurements taken at the scale of minutes or seconds). Recall that pH is negative base 10 logarithm of the molar concentration of hydrogen ions. As the pH of the solution 115 changes due to cell metabolism, the collector current ($I_C$) changes, thus enabling measurement of cell metabolism.

According to one or more embodiments of the present invention, the first well cover portion 103 and the embedded sensor portion 101 are formed of, for example, a plastic material, Polytetrafluoroethylene (PTFE), etc. In one or more exemplary embodiments of the present invention, the embedded sensor portion 101 extends perpendicularly from the first well cover portion 103. The first well cover 103 and the embedded sensor portion 101 can be formed as a unitary element or formed as separate elements connected and/or bonded together.

According to at least one exemplary embodiment of the present invention, the sensing surface 105 is disposed at an end of the embedded sensor portion 101 and/or on a sidewall of the embedded sensor portion 101. According to one or more embodiments of the present invention, the sensing surface 105 is formed of a metallic, conducting, Titanium nitride (TiN).

According to an exemplary embodiment of the present invention, the first well cover portion 103 is disposed over a well plate 102. The well plate 102 further comprises a well 104 configured to contain the sample 115, wherein the embedded sensor portion 101 extends into the well 104, and wherein at least the sensing surface 105 contacts the sample 115.

The testing system 100 is configured to measure a characteristic (e.g., metabolism) of attached cells 107 in the sample 115. For example, according to at least one embodiment of the present invention, the embedded sensor 101 of the first well cover 103 is configured as an embedded pH sensor sensing pH, which changes with metabolic action of the cells 107 attached to the well plate 102 or another substrate.

According to at least one embodiment of the present invention, a distance between sensing surface 105 and a well bottom 108 is fixed (for example, at a height of less than 0.2 millimeters (mm)). Consider that protons are generated by the cells as the result of normal metabolism processes. If the sensing surface is too far from the well bottom in the case of attached cells, pH changes can be attenuated at distance. To improve signal sensing or the responsiveness of the testing system, the sensing surface is disposed close to the cells. According to one or more embodiments of the present invention, the total solution 115 volume is small, ensuring good signal recognition.

According to one or more embodiments of the present invention, the testing system 100 further comprises a BJT transducer 109 electrically connected to the conducting wire 110 and the sensing surface 105. More particularly, a base 113 of the BJT transducer 109 is connected to the conducting wire 110. The testing system 100 further comprises a reference electrode 111 extending into the sample 115 in the well 104.

Figure 3:
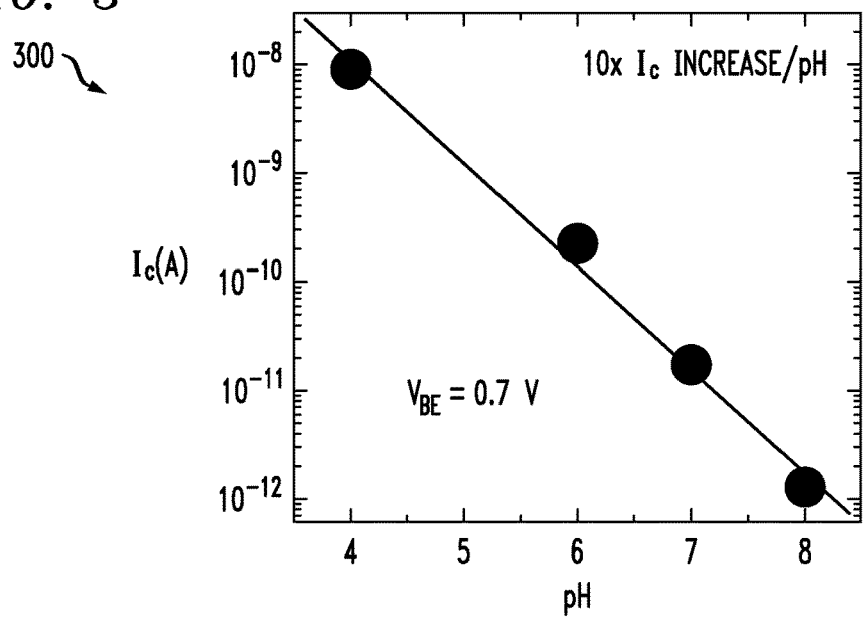
FIG. 3 is a graph of a measured collector current $I_C$ versus pH according to an embodiment of the present invention.

According to one or more embodiments of the present invention, the collector current $V_C$, which changes by about one decade (log scale) per unit of pH measure, is used to look up a corresponding pH measure (for example, using the calibration curve of FIG. 3). In one or more embodiments of the present invention, no voltmeter is needed to measure pH. According to at least one exemplary embodiment of the present invention, an automation circuit 106 can apply voltages and measure the current signals, e.g., the collector current ($V_C$). The automation circuit 106 converts raw data (e.g., the collector current ($V_C$)) into pH values using a calibration curve as shown in FIG. 3 and outputs a result for display, for example by a smart device.

According to one or more embodiments of the present invention, the automation circuit 106 includes a memory M storing a calibration curve and a processor P configured to determine a value of a property of interest given a voltage detected by the transducer and the calibration curve.

Figure 2:
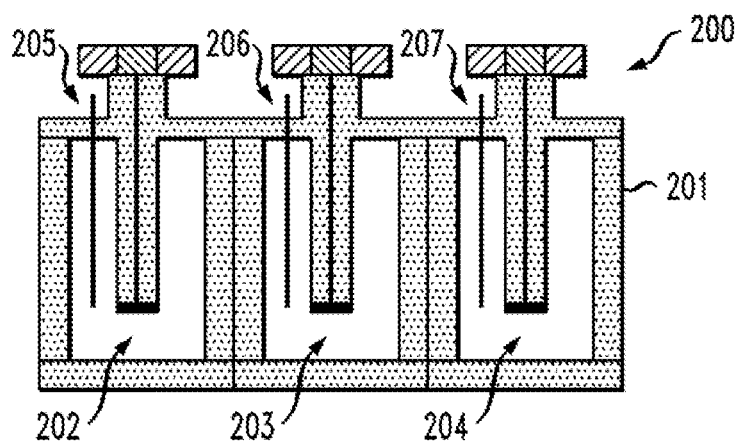
FIG. 2 depicts a view of multiple first well covers according to an embodiment of the present invention.

FIG. 2 depicts a view of a cover plate 200 for a well plate 201 according to an exemplary embodiment of the present invention. The well plate 201 comprises multiple wells 202-204. The cover plate 200 includes multiple first well cover portions 205-207 disposed over the well plate 201.

FIG. 3 is a graph 300 of a measured collector current, $I_C(A)$, versus pH according to an embodiment of the present invention. Referring again to the embedded sensor 101 and the BJT transducer 109, which comprises an emitter 112, the base 113, and a collector 114, the reference electrode 111 voltage ($V_B$) and the collector 114 voltage ($V_C$) are held at fixed voltage of 0 V ($V_B=V_C=0$ V). Emitter voltage $V_E$ is less than 0 V for a Negative-Positive-Negative (NPN) type BJT and the emitter voltage $V_E$ is greater than 0 V for Positive-Negative-Positive (PNP) BJT. The collector current ($I_C$) is the sensing signal in amperes (A). $I_C$ changes reversibly as the analyte concentration (e.g., pH) changes as shown in FIG. 3. Furthermore, cell metabolism causes pH to change with time, which is measured by the embedded BJT sensor. The pH can be determined using the collector current ($V_C$) and a known calibration curve (e.g., FIG. 3).

According to one or more embodiments of the present invention, the collector current ($V_C$) is the sensing signal current of the BJT based transducer of the testing system.

Figure 4:
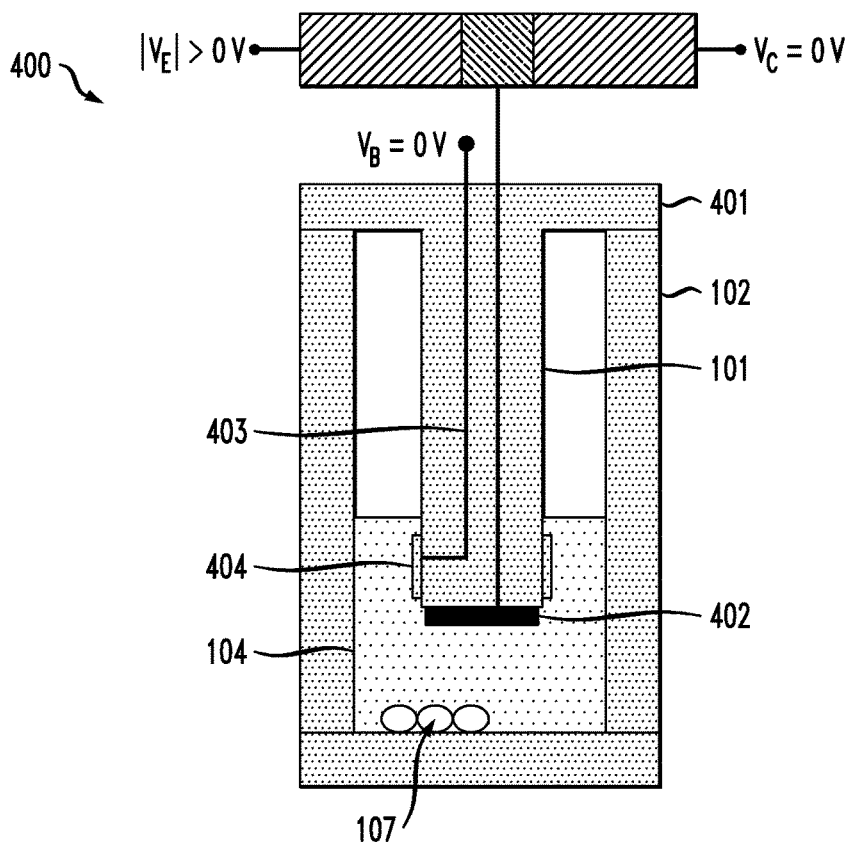
FIG. 4 depicts a view of a second well cover having an embedded sensor for measuring a characteristic of attached cells according to an embodiment of the present invention.

According to one or more embodiments of the present invention and referring to FIG. 4, a testing system 400 comprises a second well cover 401. The second well cover 401 comprises an embedded pH sensor 402. The second well cover 400 can be configured for well plate 102 comprising well 104. According to an exemplary embodiment of the present invention, a reference electrode 403 is disposed in the embedded senor 101. In at least one exemplary embodiment the reference electrode 403 is connected to a film 404 on a wall of the embedded sensor 101. The film 404 is formed of, for example, silver chloride (AgCl). According to at least one exemplary embodiment, the film 404 is replaced by a AgCl/Ag wire (not shown).

Similar to FIG. 2, the testing system 400 of FIG. 4 can be implemented over a well plate comprising multiple wells, with multiple second well covers 401 disposed over respective ones of the multiple wells.

Figure 5:
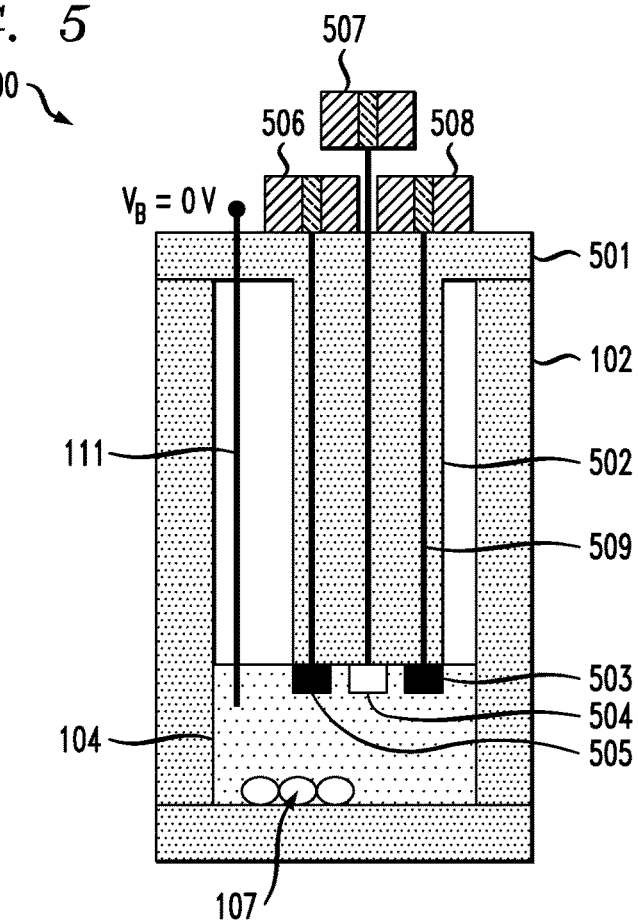
FIG. 5 depicts a view of a third well cover having a plurality of embedded sensors for measuring one or more characteristics of attached cells according to an embodiment of the present invention.

According to one or more embodiments of the present invention and referring to FIG. 5, a testing system 500 comprises a third well cover 501 disposed on well plate 102 comprising well 104. The third well cover 501 comprises one or more embedded sensors 502 embedded in the cover plate 501 for measuring attached cells. According to at least one exemplary embodiment, each embedded sensor 502 includes one or more sensing surface (503-505). According to an exemplary embodiment of the present invention, each sensing surface (503-505) binds a specific analyte (e.g., glucose, oxygen, etc.) and is connected to a respective BJT device (506-508) by respective conducting wires, e.g., 509, connecting the sensing surfaces to the bases of the BJT devices. The sensing surfaces 503-505 can be formed of TiN. The testing system 500 further comprises a reference electrode 111 extending into well 104 having cells 107 attached to the well plate 102 or another substrate.

Figure 6:
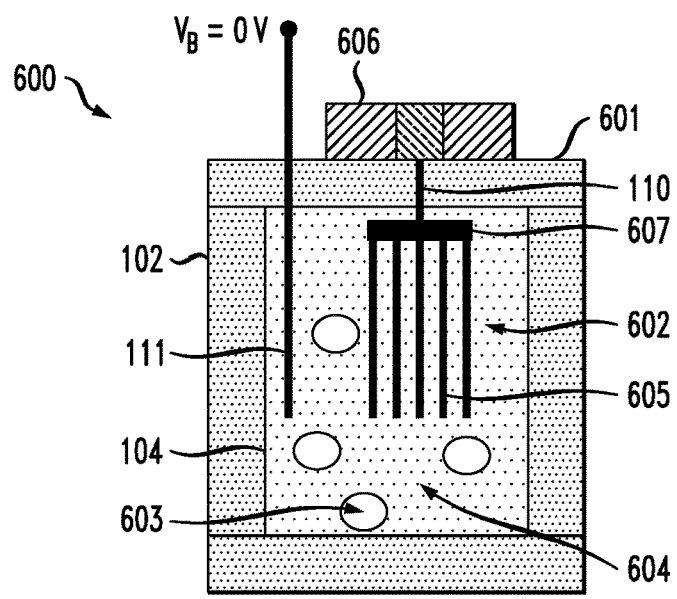
FIG. 6 depicts a view of a forth well cover having an embedded sensor for measuring a characteristic of suspended attached cells according to an embodiment of the present invention.
Figure 7:
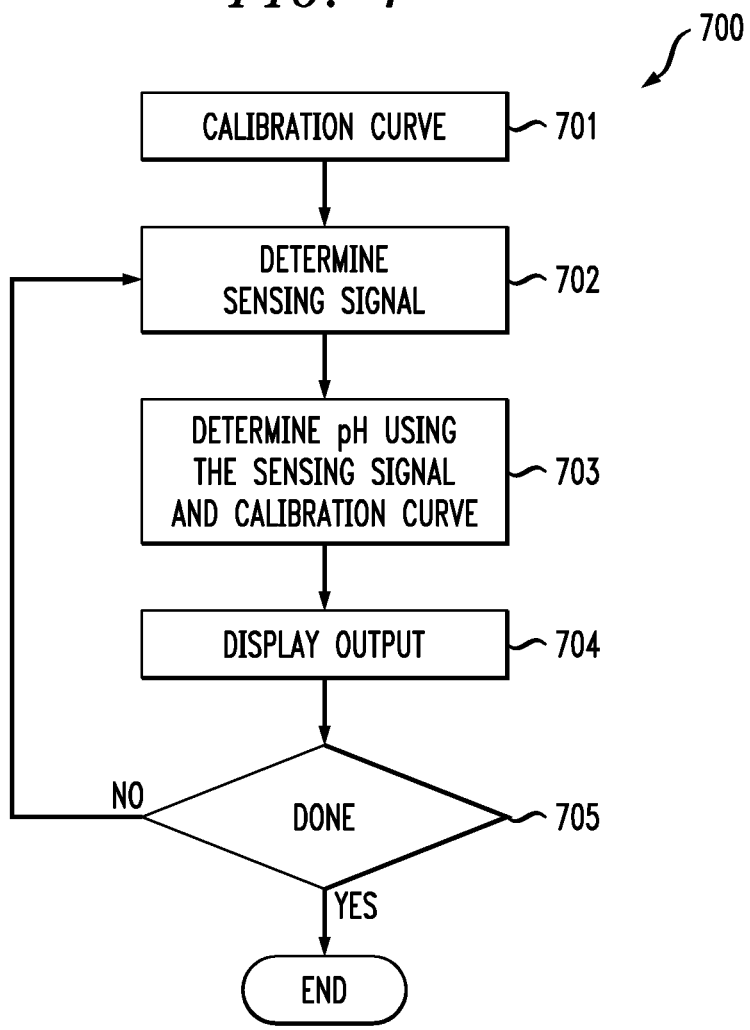
FIG. 7 is a flow diagram of a method of operating a testing system according to an exemplary embodiment of the present invention.

Suspended Cells:

According to one or more embodiments of the present invention and referring to FIG. 6, a testing system 600 comprises a fourth well cover 601 disposed on well plate 102 comprising well 104. The testing system 600 comprises an embedded sensor 602 for measuring a characteristic of cells 603 suspended in a sample 604 according to an embodiment of the present invention.

According to one or more embodiments of the present invention, a sensing surface of the embedded sensor 602 comprises one or more needles, e.g., 605.

According to one or more embodiments of the present invention, the testing system 600 further comprises a reference electrode 111 and a conduction metal 607 (e.g., wire or plate) connecting the embedded sensor 602 to a BJT device 606. According to at least one embodiment of the present invention the sensing surface of each needle is a TiN coated surface.

It should be understood in view of the foregoing detailed description that the BJT device(s), e.g., 606, can be implemented (replaced) by a field-effect transistor (FET) device, where a gate of the FET is connected to the sensing surface.

According to an embodiment of the present invention, a method of operating a testing system 700 comprises generating a calibration curve 701 for a property of interest (e.g., current vs. pH of a sample), determining a sensing signal generating by a sample 702, determining the property of interest (e.g., pH) of the sample using the sensing signal and the calibration curve 703, displaying an output of the determination 704 (e.g., building a graph of the property of interest over time), and determining an end of test 705 (e.g., based on elapsed time, change in the monitored property of interest is less than a threshold, or reaching a predetermined end condition of the property). It should be understood that the calibration curve can be stored in a memory and provided at block 701; the calibration curve need not be generated for each test. It should also be understood that the output 704 can further include a detection of a certain condition. For example, as described herein, cancerous cells have relatively high metabolism and will be associated with lower pH values in a sample. Such a detection can be output at block 704.

Recapitulation:

According to one or more embodiments of the present invention, a testing system 100 comprises a well cover portion 103, a sensor portion 101 extending from the well cover portion, a sensing surface 105 disposed on the sensor portion, a conducting wire 110 extending through the sensor portion and contacting the sensing surface, a transducer 109 connected to the conducting wire, and a reference electrode 111 extending through the well cover portion.

According to one or more embodiments of the present invention, a testing system 600 comprises a well cover portion 601, a conducting wire 110 extending through the well cover portion, a sensing surface 605 electrically connected to the conducting wire, a transducer 606 connected to the conducting wire, and a reference electrode 111 extending through the well cover portion.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A testing system comprising:
    a well cover portion;
    a sensor portion extending from the well cover portion;
    a sensing surface disposed on the sensor portion;
    a conducting wire extending through the sensor portion and contacting the sensing surface;
    a transducer connected to the conducting wire; and
    a reference electrode extending through the well cover portion.

2. The testing system of claim 1, further comprising an automation circuit connected to the transducer and the reference electrode.

3. The testing system of claim 2, wherein the automation circuit further comprises:
    a memory storing a calibration curve; and
    a processor configured to determine a value of a property of interest given a sensing signal current detected by the transducer and the calibration curve.

4. The testing system of claim 1, further comprising a well plate having a well, wherein the sensor portion extends into a well of the well plate and contacts a sample in the well.

5. The testing system of claim 1, wherein the transducer is one of a bipolar junction transistor and a field-effect transistor.

6. The testing system of claim 1, wherein the transducer is one of a plurality of transducers, wherein each of the plurality of transducers is connected to a respective sensing surface by a respective conducting wire.

7. The testing system of claim 6, wherein at least two of the sensing surfaces are configured to detect a different property of interest of a sample in the well.

8. The testing system of claim 1, wherein the sensor portion comprises a plurality of needles connected to the conducting wire.

9. The testing system of claim 8, wherein the sensing surface of each of the plurality of needles is titanium nitride.

10. The testing system of claim 1, further comprising a film disposed on the sensor portion and connected to the reference electrode.

11. The testing system of claim 10, wherein the film is formed of one of silver chloride or silver.

12. The testing system of claim 10, wherein the reference electrode is disposed in the sensor portion.

13. The testing system of claim 1, wherein the reference electrode extends from the well cover portion is disposed apart from the sensor portion.

14. A testing system comprising:
a well cover portion;
a conducting wire extending through the well cover portion;
a sensing surface electrically connected to the conducting wire;
a transducer connected to the conducting wire; and
a reference electrode extending through the well cover portion.

15. The testing system of claim 14, further comprising a conduction metal disposed between the conducting wire and the sensing surface.

16. The testing system of claim 15, wherein the sensing surface extends from the conduction metal and comprises at least one needle.

17. The testing system of claim 14, further comprising an automation circuit connected to the transducer and the reference electrode.

18. The testing system of claim 17, wherein the automation circuit further comprises:
a memory storing a calibration curve; and
a processor configured to determine a value of a property of interest given a voltage detected by the transducer and the calibration curve.

19. The testing system of claim 1, further comprising a well plate having a well, wherein the sensing surface extends into a well of the well plate and contacts a sample in the well.

20. The testing system of claim 8, wherein the sensing surface is titanium nitride.

* * * * *